United States Patent (10) Patent No.: US 7,730,796 B2
Shimada et al. (45) Date of Patent: Jun. 8, 2010

(54) METHOD FOR SAMPLING FLUE GAS FOR ANALYSIS CONTAINING GAS COMPONENT HAVING HIGH SUSCEPTIBILITY TO ADSORPTION (75) Inventors: Hiroshi Shimada, Hiroshima (JP); Shinya Tamura, Hiroshima (JP); Naoyuki Tokunaga, Hiroshima (JP); Megumi Kikkawa, Iwakuni (JP)

(73) Assignee: The Chugoku Electric Power Co., Inc., Hiroshima (JP)

( * ) Notice: Subject to any disclaimer, the term of this patent is extended or adjusted under 35 U.S.C. 154(b) by 482 days.

(21) Appl. No.: 11/547,029

(22) PCT Filed: Apr. 1, 2004

(86) PCT No.: PCT/JP2004/004813

§ 371 (c)(1),
(2), (4) Date: Oct. 2, 2006

(87) PCT Pub. No.: WO2005/100947

PCT Pub. Date: Oct. 27, 2005

(65) Prior Publication Data

US 2007/0193374 A1 Aug. 23, 2007

(51) Int. Cl.
*G01N 1/10* (2006.01)
(52) U.S. Cl. .............. 73/863.83; 73/863.81; 73/863.12
(58) Field of Classification Search . 73/863.11–863.12, 73/863.81, 863.83
See application file for complete search history.

(56) References Cited

U.S. PATENT DOCUMENTS 3,592,562 A * 7/1971 Spliethoff ................ 73/863.12
4,336,722 A * 6/1982 Schweitzer ............... 73/863.12
5,759,482 A * 6/1998 Gregory et al. ............... 266/79
5,824,919 A * 10/1998 Hansen ..................... 73/863.23
6,022,510 A * 2/2000 Springmann ............. 73/863.12
2003/0000189 A1 * 1/2003 Honda et al. .................. 55/524

FOREIGN PATENT DOCUMENTS

| JP | 61-40537 A | 2/1986 |
| JP | 8-210954 A | 8/1996 |
| JP | 2001-83054 A | 3/2001 |
| JP | 3229088 B2 | 9/2001 |
| JP | 3322420 B2 | 6/2002 |
| JP | 2004-117271 A | 4/2004 |

* cited by examiner

*Primary Examiner*—Hezron Williams
*Assistant Examiner*—Nashmiya S Fayyaz
(74) *Attorney, Agent, or Firm*—Sughrue Mion, PLLC (57) ABSTRACT An object of the invention is to realize high-accuracy analysis of a flue gas in terms of a trace amount of ammonia so as to control the level of ammonia gas to be added to a flue gas $NO_x$ removal apparatus. Since the ammonia gas to be determined is a highly absorbable, the gas component is considerably adsorbed on a surface of the flue gas sampling tube during sampling of flue gas. When a conventional sampling method including heating a gas sampling tube is employed, the amount of sampled gas is reduced through adsorption during gas sampling, failing to obtain concentration values at high accuracy. Thus, a high-accuracy gas sampling method replacing a conventional, heating-based method includes completely washing out, with an absorption liquid therefor serving as a washing liquid, a target ammonia gas deposited on the inner wall of a flue gas sampling tube (2), whereby the gas component is thoroughly collected. Through analysis of the thus-obtained washing liquid, high-accuracy analysis can be attained.

1 Claim, 6 Drawing Sheets

Low concentration
Comparison with JIS method (B-A)

| Concentration difference PPM | Heating-based method 1 Average −2.5 | | Method of the invention Average 1.4 | |
|---|---|---|---|---|
| | Occurrence | SD 0.8 | Occurrence | SD 1.4 |
| 6~ | 0 | | 0 | |
| 4~5 | 0 | | 1 | |
| 2~3 | 0 | | 3 | |
| 0~1 | 0 | | 5 | |
| −2~−1 | 5 | | 0 | |
| −4~−5 | 5 | | 0 | |
| ~−6 | 0 | | 0 | |

METHOD FOR SAMPLING FLUE GAS FOR ANALYSIS CONTAINING GAS COMPONENT HAVING HIGH SUSCEPTIBILITY TO ADSORPTION

TECHNICAL FIELD

The present invention relates to a method for sampling an analyte flue gas containing a gas component having high susceptibility to adsorption (i.e., having high adsorbability). The method is provided in order to realize high-accuracy determination of a small amount of ammonia gas contained in flue gas, and the thus-obtained analytical data are employed for regulating the level of ammonia gas added to a flue gas $NO_x$ removal apparatus.

BACKGROUND ART

Conventionally, gas component analysis of flue gas has been generally carried out through wet-format analysis including in situ sampling of analytes from the flue gas or through gas monitoring. In the flue gas analysis, gas components such as nitrogen oxides and sulfur oxides can be sampled in a sampling step without particular technical problems, and can be readily determined at a target accuracy.

The gas components to be determined in the invention, such as ammonia gas, are highly absorbable. These gas components are considerably adsorbed on the inner wall of a flue gas sampling tube during sampling of flue gas. Thus, when a conventional sampling method is employed, a portion of the sampled gas is adsorbed on the inner wall of the tube and remains in the tube, failing to obtain measurements of high accuracy.

In order to solve the above problem, hitherto, such problematic adsorption has been generally mitigated through heating a gas sampling tube. In addition, JIS K0099 stipulates a flue gas ammonia analysis method, in which measures against gas adsorption, such as heating a flue gas introduction tube, are taken. The method stipulated by JIS K0099 is a standard method employed, through manual operations, in an ordinary-scale facility at which flue gas is sampled.

In the case where automatic, continuous gas monitoring is performed in a flue gas sampling site such as a comparatively large-scale flue gas of a boiler placed in a power plant, the present inventors previously employed a gas sampling method in which a flue gas sampling tube equipped with a large-scale heating mechanism is employed, and a large amount of flue gas is introduced through suction to an auto-analyzer. The method is disclosed in Japanese Patent Nos. 3229088 and 3322420.

However, when the above method is employed, problematic adsorption of gas components occurs due to insufficient heating of a gas sampling tube or an insufficiently heated zone of the tube. Therefore, the method is unsatisfactory when applied to a micro-analysis for determining a concentration of about 100 to about 1 ppm at high accuracy. The adsorption causes loss of the gas component(s) to be analyzed.

Specifically, in the above method, a flue gas is introduced, through suction, into an absorption liquid which absorbs ammonia contained in the flue gas, and the amount of ammonia trapped in the absorption liquid is determined, thereby obtaining the ammonia content of the flue gas. In this step, a portion of ammonia gasp is adsorbed on a surface of the gas sampling tube or other relevant sections. Thus, the adsorbed gas component(s) cannot be trapped in the absorption bottle.

When the above phenomena occur, the obtained analytical values become smaller than expected. Under such circumstances, the present invention is directed to an improvement of the flue gas sampling tube section disclosed in Japanese Patent Nos. 3229088 and 3322420.

Ammonia is a highly water-soluble component and is readily adsorbed on a gas sampling tube. Therefore, upon sampling of ammonia, a sampling tube is generally heated in order to suppress dew formation of water and adsorption of ammonia. In this case, the entirety of the gas sampling tube must be sufficiently heated so as to completely heat insufficiently heated sections. Thus, in order to attain sufficient heating effect particularly in connection portions and a similar portion of the sampling tube, know-how and skills therefor are needed.

The aforementioned conventional methods are unsatisfactory for the micro-component analysis of flue gas. Thus, an object of the present invention is to provide a more reliable gas sampling method, through collecting a gas component deposited on a surface of a flue gas sampling tube, thereby enhancing analysis accuracy.

DISCLOSURE OF THE INVENTION

The present invention provides a gas sampling method in which deterioration in analysis accuracy which would otherwise be caused by deposition of a gas component onto a surface of a sampling tube is prevented during sampling. According to the method, the inner surface of a sampling tube is washed with washing water, and the resultant wash liquid is combined with a sample liquid, whereby a combined sample liquid containing a sampled gas component and the gas component deposited onto the inner surface of the sampling tube is provided. Through analysis of the sample liquid, the entirety of the analyte gas component can be determined and, as a result, analysis accuracy in microanalysis can be remarkably enhanced.

In order to provide a gas analyzing apparatus which realizes automatic washing of a gas sampling tube, while the sampling tube is attached to a flue gas tube during gas sampling, the sampling tube is required to have a structure highly suitable for the purpose. Specifically, the structural requirements are as follows: the gas sampling tube has a double-tube structure; washing water is introduced into a space between the inner tube and the outer tube; a small through hole for introducing the wash water into the sampling tube is provided at a position on the inner tube that faces the outer tube; a flue gas can be collected in a gas absorption bottle through suction by means of a flue gas suction pump; and the washing water is forcedly introduced into the flue gas sampling tube by means of a pump. Furthermore, according to the present invention, the aforementioned gas sampling is performed through controlling of conditions such as the position of a small through hole through which washing water is fed, amount of washing water, and washing time.

Reference numerals shown in the drawings will next be described. The reference numerals are employed in accordance with needs in the description of the invention provided hereinbelow.

| | |
|---|---|
| 1 | Flue |
| 2 | Sampling tube |
| 3 | Flue gas |
| 4 | Inner tube |
| 5 | Outer tube |
| 6 | Small through hole |
| 7 | Flange |
| 8 | Sealing |
| 9 | Washing liquid inlet |
| 10 | Gas suction inlet |
| 11 | Washing liquid pump |
| 12 | Gas absorption bottle |
| 13 | Washing liquid |
| 14 | Suction pump |
| 15 | Gas meter |

BEST MODES FOR CARRYING OUT THE INVENTION

Figure 1:
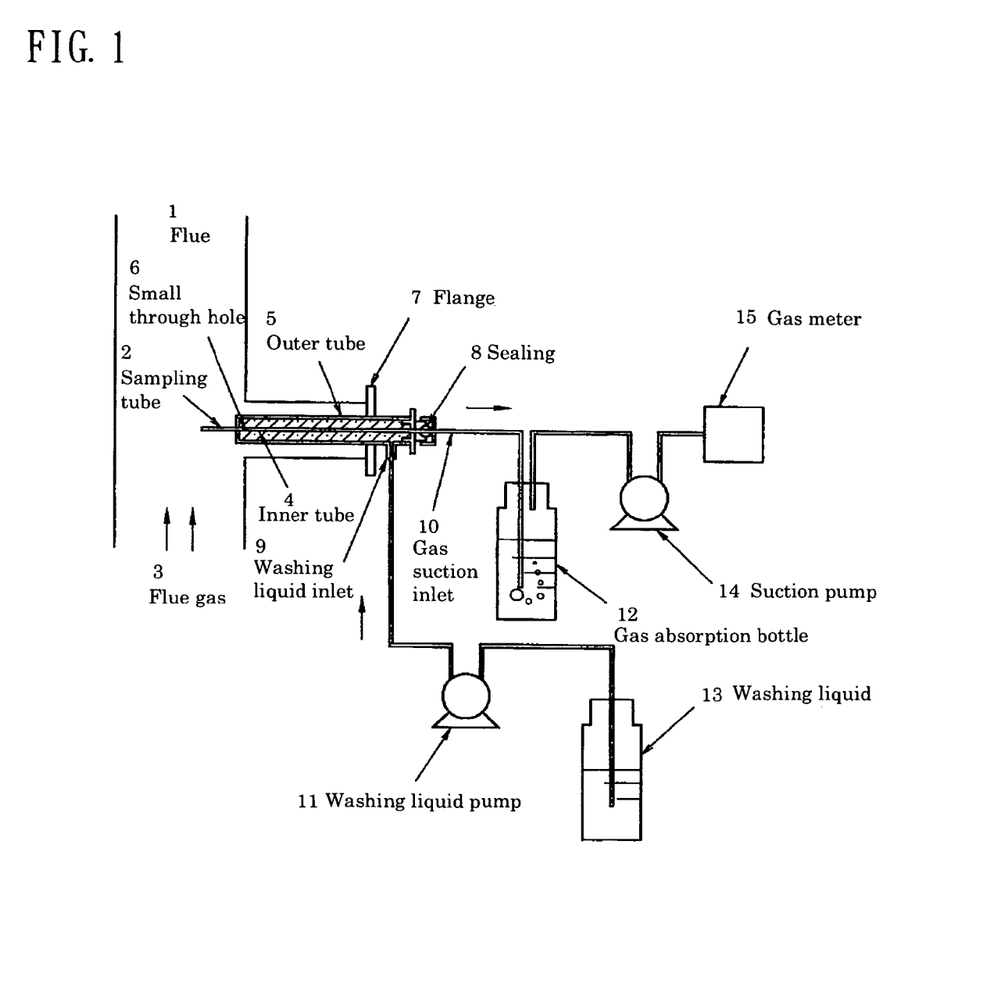
FIG. 1 is a schematic configuration showing an embodiment of the flue gas sampling method of the present invention.
Figure 2:
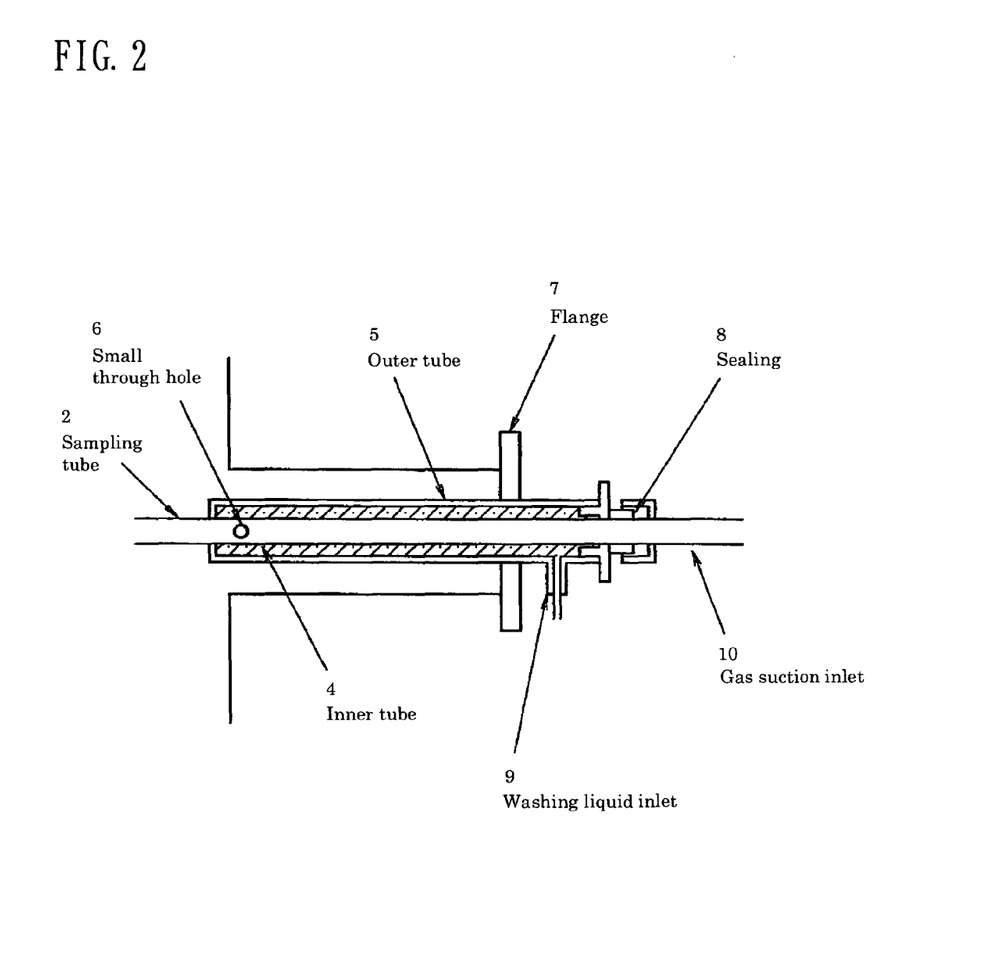
FIG. 2 is an enlarged view of the flue gas sampling tube in FIG. 1 showing the embodiment of the flue gas sampling method of the present invention.

Hereinafter, an embodiment of the present invention will be described in detail with reference to the drawings. FIG. 1 is a schematic configuration of an automated measuring apparatus according to the present invention. FIG. 2 is an enlarged view of the gas sampling tube section. A tip section of a gas sampling tube (2), having a single tube structure, is caused to be contact with flue gas (3) flowing through a flue (1). The gas sampling tube is made of a material which withstands high temperature of flue gas, generally made of stainless steel. The gas sampling tube has a diameter of about 5 mm.

A section of the gas sampling tube extending from a section outside the flue to the position of a flange (7) has a double-tube structure (4, 5). The gas sampling tube (2) is connected to a flue gas absorption bottle (12), which is further connected to a suction pump (14) and a gas flow meter (15). A sample liquid which has absorbed the flue gas component of interest is automatically collected and transferred to an automatic analyzer (not illustrated).

Washing liquid is injected into a space between the inner tube and the outer tube (i.e., the inside of the double-tube structure (4, 5)). The washing liquid is fed by means of a washing liquid pump (11) and injected through a washing liquid inlet (9) disposed on the downstream side of the double-tube structure (4, 5).

The gas sampling procedure will next be described. Through operation of the flue gas suction pump (14), flue gas flowing through the flue (1) is drawn through suction. The flue gas passes the sampling tube and transferred to the gas absorption bottle (12), where an analyte gas component (ammonia, in this case) is absorbed. After completion of absorption, the flue gas is further drawn through suction and discharged via the gas meter (15).

Just before completion of sampling in a predetermined amount of flue gas, the washing liquid pump (11) is operated, while the flue gas suction pump (14) is continuously operated, whereby the washing liquid (13) is injected into the double-tube structure of the gas sampling tube.

However, depending on the condition of flue gas passage tube (e.g. dew formation of water during the course of gas sampling), the washing liquid pump (11) may be operated during the course of sampling a flue gas in a predetermined amount, whereby formed dew of water can be discharged with the washing liquid. In this case, the flue gas suction pump (14) is continuously operated.

The washing liquid is fed into the double-tube structure (4, 5) provided between the inner tube and the outer tube, and injected into the inner tube (i.e., the inside of the flue gas sampling tube (2)) through a small through hole (6) provided in the tip section of the tube.

Thereafter, the washing liquid flows downstream in a flue gas passage tube for about 10,000 mm, and collected with an absorption liquid.

The washing liquid which has been injected into the flue gas sampling tube is transferred to the gas absorption bottle (12) through suction by means of the operating flue gas suction pump (14). Through this procedure, the inner surface of the sampling tube is washed and, as a result, the ammonia component deposited onto the inner surface is transferred to the gas absorption bottle (12), where the ammonia component is combined with the absorption liquid which has already absorbed ammonia from the flue gas. Thus, through washing of the inner surface of the sampling tube, ammonia can be more effectively and reliably collected.

The phenomenon occurring in the double-tube structure of the flue gas sampling tube will further be described. A tip section of the double tube that faces the flue gas is heated to 200 to 300° C. through contact with flue gas. In an initial stage of injection of a washing liquid, the washing liquid (pure water, in this case) boils in the section. The thus-generated steam is drawn through the small through hole (6) in the gas suction direction. During passage of the pipe, the steam is cooled, and formed water is collected in the absorption bottle.

When the washing liquid is continuously injected, the entirety of the double tube is cooled. Then, the washing liquid is injected through the small through hole (6) in the form of liquid. The washing liquid is collected in the absorption bottle, whereby ammonia (hereinafter represented by $NH_3$) is captured.

Among flue gas components analyzed through the embodiment of the invention, analysis accuracy of $NH_3$ gas will next be described. Flue gas sampling experiments were carried out at a large-scale flue which is connected to a boiler provided in a thermal power station equipped with an $NO_x$ removal apparatus. Three different sampling tubes were installed at the corresponding flue gas sampling holes disposed in the same flange. Each sampling tube had a tip section extending the flue and having a length of 1,150 mm. Sampling time, sampling intervals, and other conditions were fixed. The sampling method of the present invention, which is included in a continuous gas measuring method, was compared with conventional heating-based sampling methods; i.e., methods disclosed in Japanese Patent Nos. 3229088 and 3322420. As a reference sampling method (manual analysis), the JIS K0099 method was also performed. Each of three continuous methods was carried out simultaneously with the JIS method.

Figure 3:
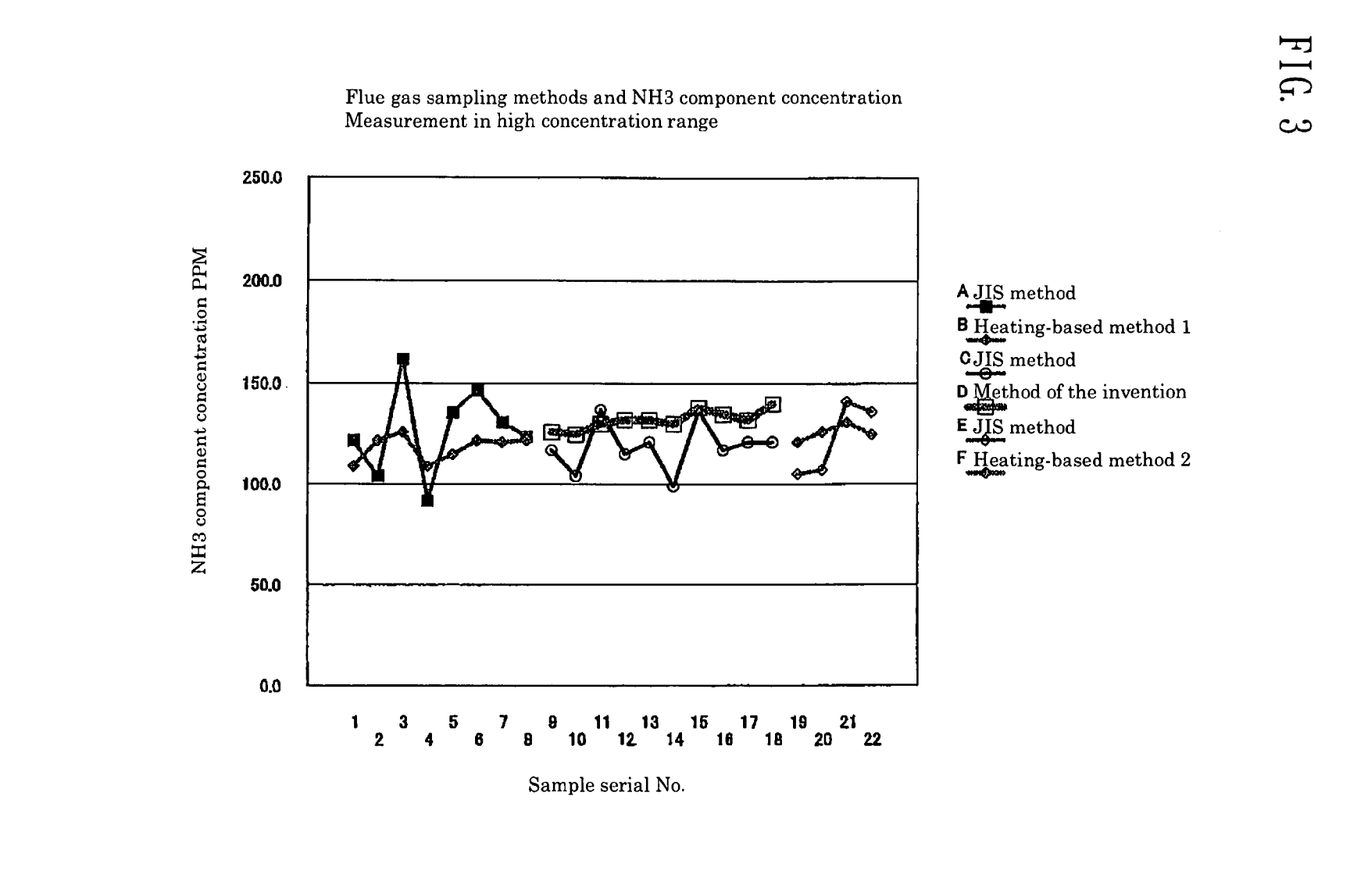
FIG. 3 is a graph showing results of an $NH_3$ gas (high concentration) sampling test carried out according to an embodiment of the flue gas sampling method of the present invention, as well as the results of other gas sampling tests.
Figure 4:
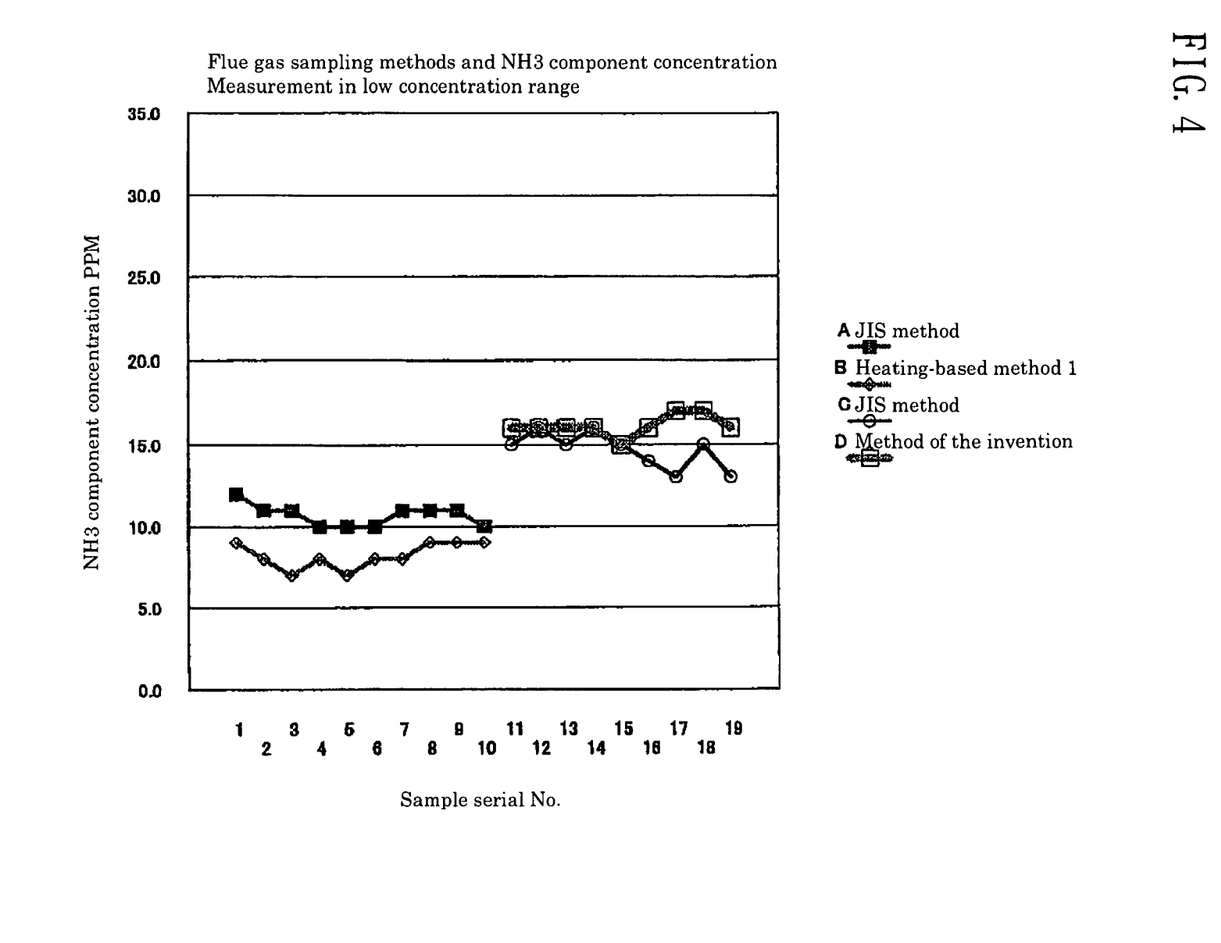
FIG. 4 is a graph showing results of an $NH_3$ gas (low concentration) sampling test carried out according to an embodiment of the flue gas sampling method of the present invention, as well as the results of other gas sampling tests.

The heating-based methods were carried out under two different heating conditions. The flue gas sampling conditions of the above methods are shown in Table 1. The results of the experiments performed under the above conditions are shown in Table 2, FIG. 3, Table 3, and FIG. 4. Table 2 and FIG. 3 show the results of experiments carried out under comparatively high $NH_3$ concentration (about 130 ppm). Sampling was continuously performed in order to avoid variation of sampling conditions, and the sampling trials are represented by serial test numbers. Each of the continuous methods was carried out simultaneously with the JIS method (manual analysis). Table 3 and FIG. 4 show the results of experiments carried out under comparatively low $NH_3$ concentration (about 15 ppm).

TABLE 1

Flue gas sampling conditions
Flue gas conditions
Flue gas temperature: about 350° C.
Dust content: about 10 g/m³

|  | Continuous determination | Heating-based method | | Manual determination |
|---|---|---|---|---|
|  | Method of the invention | Heating 1 | Heating 2 | JIS method |
| Sampled gas flow | 2 L/min | Sampling tube 12 L/min Introducing tube 2 L/min | Sampling tube 12 L/min Introducing tube 2 L/min | 2 L/min |
| Heating | No | 250° C. | 300° C. | No |
| Sampling tube washing | Yes | No | No | Yes |
| Sample amount | 10 L | 10 L | 10 L | 10 L |
| Absorbing liquid | Boric acid solution (5 g/L) | Boric acid solution (5 g/L) | Boric acid solution (5 g/L) | Boric acid solution (5 g/L) |
| Absorbing liquid (amount) | 50 mL | 50 mL | 50 mL | 50 mL |
| Washing liquid | about 150 mL | No | No | about 100 mL |
| Analyte solution | 250 mL | 250 mL | 250 mL | 250 mL |
| Pre-analysis dust removal | | Membrane filtration | | |
| Analysis | | Ion chromatography | | |

TABLE 2

Test results (high concentration range)

| Serial test No. | Continuous determination Method of the invention and heating-based methods | | Manual determination JIS | Comparison |
|---|---|---|---|---|
| | | Concentration A PPM | Concentration B PPM | B − A PPM |
| 1 | Heating-based | 109.0 | 122.0 | −13.0 |
| 2 | method 1 | 122.0 | 104.0 | 18.0 |
| 3 | | 126.0 | 162.0 | −36.0 |
| 4 | | 109.0 | 92.0 | 17.0 |
| 5 | | 115.0 | 136.0 | −21.0 |
| 6 | | 122.0 | 147.0 | −25.0 |
| 7 | | 121.0 | 131.0 | −10.0 |
| 8 | | 122.0 | 124.0 | −2.0 |
| 9 | Method of the | 126.0 | 117.0 | 9.0 |
| 10 | invention | 125.0 | 104.0 | 21.0 |
| 11 | | 130.0 | 137.0 | −7.0 |
| 12 | | 132.0 | 115.0 | 17.0 |
| 13 | | 132.0 | 121.0 | 11.0 |
| 14 | | 130.0 | 99.0 | 31.0 |
| 15 | | 138.0 | 137.0 | 1.0 |
| 16 | | 135.0 | 117.0 | 18.0 |
| 17 | | 132.0 | 121.0 | 11.0 |
| 18 | | 140.0 | 121.0 | 19.0 |
| 19 | Heating-based | 121.0 | 105.0 | 16.0 |
| 20 | method 2 | 126.0 | 107.0 | 19.0 |
| 21 | | 131.0 | 141.0 | −10.0 |
| 22 | | 125.0 | 136.0 | −11.0 |

TABLE 3

Test results (low concentration range)

| Serial test No. | Continuous determination Method of the invention and heating-based method | | Manual determination JIS | Comparison |
|---|---|---|---|---|
| | | Concentration A PPM | Concentration B PPM | B − A PPM |
| 1 | Heating-based | 9.0 | 12.0 | −3.0 |
| 2 | method 1 | 8.0 | 11.0 | −3.0 |
| 3 | | 7.0 | 11.0 | −4.0 |
| 4 | | 8.0 | 10.0 | −2.0 |
| 5 | | 7.0 | 10.0 | −3.0 |
| 6 | | 8.0 | 10.0 | −2.0 |
| 7 | | 8.0 | 11.0 | −3.0 |
| 8 | | 9.0 | 11.0 | −2.0 |
| 9 | | 9.0 | 11.0 | −2.0 |
| 10 | | 9.0 | 10.0 | −1.0 |
| 11 | Method of the | 16.0 | 15.0 | 1.0 |
| 12 | invention | 16.0 | 16.0 | 0.0 |
| 13 | | 16.0 | 15.0 | 1.0 |
| 14 | | 16.0 | 16.0 | 0.0 |
| 15 | | 15.0 | 15.0 | 0.0 |
| 16 | | 16.0 | 14.0 | 2.0 |
| 17 | | 17.0 | 13.0 | 4.0 |
| 18 | | 17.0 | 15.0 | 2.0 |
| 19 | | 16.0 | 13.0 | 3.0 |

Figure 5:
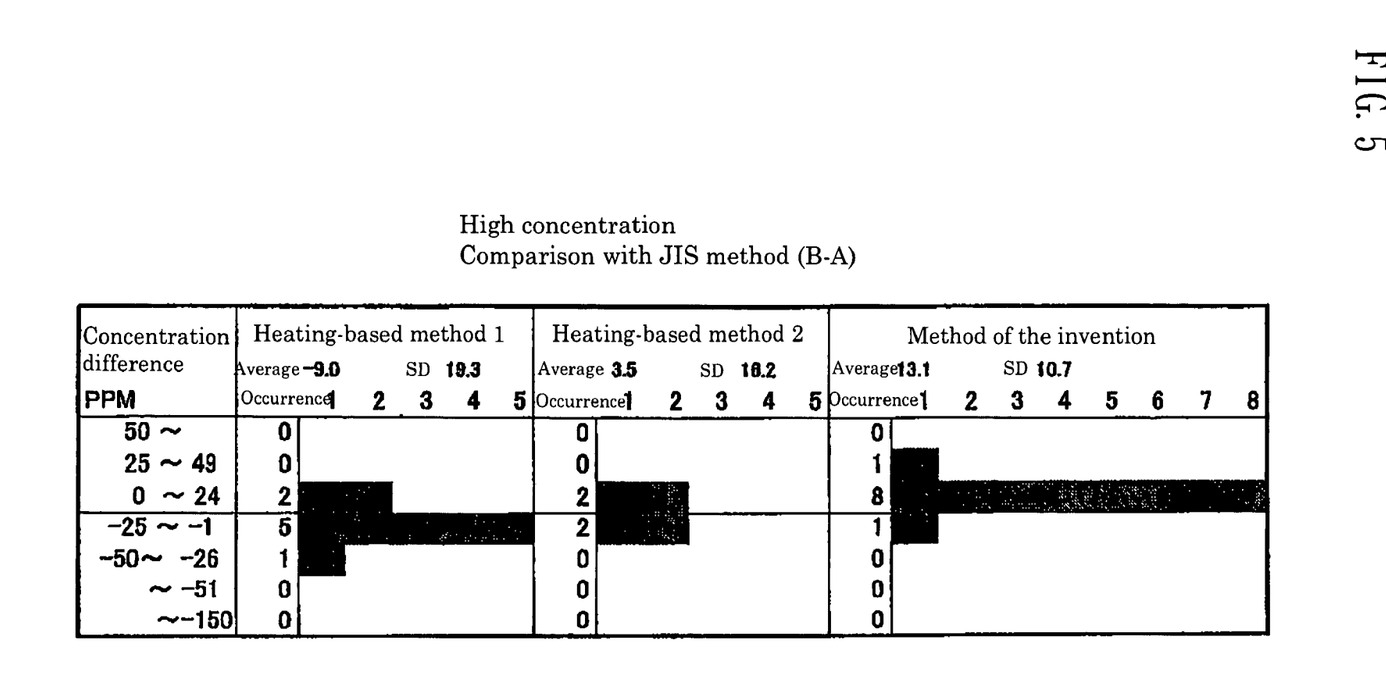
FIG. 5 is a histogram showing results of $NH_3$ gas (high concentration) sampling tests carried out according to an embodiment of the flue gas sampling method of the present invention and to comparative methods.
Figure 6:
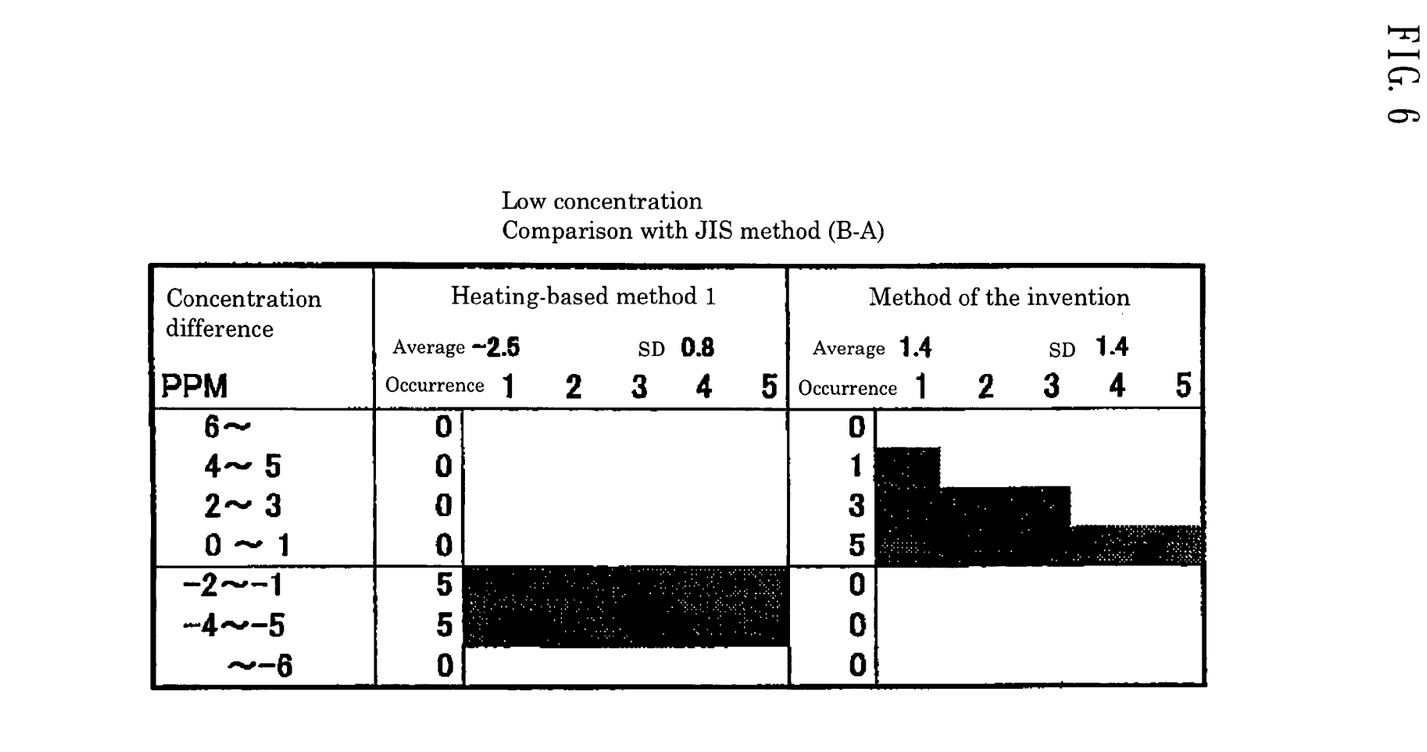
FIG. 6 is a histogram showing results of $NH_3$ gas (low concentration) sampling tests carried out according to an embodiment of the flue gas sampling method of the present invention and to comparative methods.

The obtained data are more clearly shown in FIGS. 3 and 4. For the purpose of better understanding, FIGS. 5 and 6 show histograms indicating difference between concentration determined through the continuous method and that determined though the JIS method. As shown in FIG. 5, when heating-based method 1 was employed for high-concentration range analysis, the obtained concentration values were smaller than those obtained through the JIS method. These smaller values may be attributable to failure to completely capture $NH_3$. The continuous determination method provided reliable measurements.

Heating-based method 2 provided concentration values almost equivalent to those obtained through the JIS method, indicating that method 2 attained more effective heating as compared to method 1. The method of the present invention provided concentration values considerably higher than those obtained through the JIS method, indicating that the method of the invention attained sufficient capturing of $NH_3$. Similar to the case of high-concentration range analysis, as shown in FIG. 6, heating-based method 1 provided smaller concentration values in a low-concentration range, but the method of the invention attain high concentration values. Therefore, the method of the present invention has been found to be remarkably suitable for determination of $NH_3$ gas concentration, from low to high concentration range.

INDUSTRIAL APPLICABILITY

As described hereinabove, according to the flue gas sampling method of the present invention, the ammonia gas component concentration of flue gas can be determined at remarkably high accuracy. As shown in FIGS. 3 to 6, the method of the present invention is remarkably excellent as compared with conventional methods. Through combination of the method of the invention with an automatic analyzer for continuous determination, the automatic analyzer will be of great value.

The invention claimed is:

1. In relation to an automated flue gas measurement apparatus, a method for sampling an analyte flue gas containing a gas component having high adsorbability, characterized in that the method comprises:

providing a gas sampling tube having a double-tube structure including an inner tube and an outer tube;

causing a sampled gas to flow through the inner tube;

injecting, into a space between the inner tube and the outer tube, a washing liquid for washing out a flue gas component deposited on a surface of the inner tube;

introducing the washing liquid, through a small through hole provided at a position on the inner tube that faces the outer tube, into the inner tube through which flue gas passes;

in a gas sampling mode, collecting the washing liquid in a flue gas absorption bottle using a flue gas suction pump disposed downstream of the gas sampling tube to thereby collect a predetermined amount of the flue gas component deposited on the surface of the gas sampling tube; and in a washing mode, operating a washing liquid pump so as to inject washing liquid only after collection of flue gas in the flue gas absorption bottle in the predetermined amount as determined by a gas meter.

* * * * *